United States Patent [19]

Yim et al.

[11] Patent Number: 4,853,218

[45] Date of Patent: Aug. 1, 1989

[54] ZINC-PROTAMINE-ALPHA INTERFERON COMPLEX

[75] Inventors: Zachary Yim, Paramus; Michael A. Zupon, Basking Ridge; Imtiaz A. Chaudry, Denville, all of N.J.

[73] Assignee: Schering Corporation, Kenilworth, N.J.

[21] Appl. No.: 18,243

[22] Filed: Feb. 24, 1987

[51] Int. Cl.$^4$ ........................................ A61K 45/02

[52] U.S. Cl. ................................ 424/85.7; 424/85.4

[58] Field of Search ................ 424/85, 85.7; 530/351

[56] References Cited

U.S. PATENT DOCUMENTS

| | | | |
|---|---|---|---|
| 3,912,807 | 10/1975 | Alhern et al. | 424/178 |
| 4,289,690 | 9/1981 | Pestka et al. | 424/85 |
| 4,496,537 | 1/1985 | Kwan | 424/85 |
| 4,605,555 | 9/1984 | Sato et al. | 424/85 |

FOREIGN PATENT DOCUMENTS

| | | |
|---|---|---|
| 0032134 | 7/1981 | European Pat. Off. . |
| 0051873 | 5/1982 | European Pat. Off. . |

OTHER PUBLICATIONS

CA, vol. 103, No. 13, Sep. 30, 1985, Abst. 99718v.

Nagata et al., *Nature*, vol. 284, pp. 316–320.

Rubenstein, *Biochimica et Biophysica Acta*, 696 (1982) pp. 5–16.

*U.S. Pharmacopeia*, 16th ed., (1985), pp. 540–541, 2007.

*Primary Examiner*—Blondel Hazel

*Attorney, Agent, or Firm*—Anita W. Magatti; James R. Nelson; Stephen I. Miller

[57] ABSTRACT

An insoluble zinc-protamine alpha interferon complex useful as an injectable sustained release dosage form for administering alpha interferon is disclosed.

10 Claims, No Drawings

ZINC-PROTAMINE-ALPHA INTERFERON COMPLEX

SUMMARY OF THE INVENTION

The present invention relates to an insoluble zinc-protamine-alpha interferon complex useful as an injectable sustained release dosage form for administering alpha interferon.

BACKGROUND

Injectable pharmaceutical formulations are well known in the art. See *Remington's Pharmaceutical Sciences,* Mack Publishing Company, Easton, PA, 16th Edition, 1980. Usually such formulations are in the form of dispersions such as colloids, emulsions and suspensions. More recently, sustained release injectable formulations comprising polymers have been used.

Typical sustained release injectable formulations include aqueous or water-miscible suspensions, but such suspensions often present stability problems and may not provide long enough retention time of the active in the formulation, either because the dispersion breaks down or because the dispersion is too soluble in the surrounding body fluids (e.g., the blood and lymph systems).

An example of a successful aqueous-based sustained release suspension is the protamine-zinc-insulin suspension. The United States Pharmacopeia (USP) entry for the suspension indicates a standard formulation as containing 40–100 USP Insulin Units/ml of an aqueous solution of zinc (0.15 to 0.25 mg zinc/100 USP Insulin Units) and protamine (1 to 1.5 mg protamine/100 USP Insulin Units) at pH 7.1 to 7.4. Typically the pH is maintained by 0.15 to 0.25% (w/v) dibasic sodium phosphate and the formulation also contains 1.4 to 1.8% (w/v) glycerin and 0.18 to 0.22% (w/v) cresol or 0.22 to 0.28% (w/v) phenol. Depending on the insulin concentration and the response of the patient, one injection releases insulin for up to three days.

Interferons are a family of proteins which exhibit antiviral activity against certain viruses and anticancer activity against certain cancers. Interferons include natural or recombinant alpha (leucocyte), beta (fibroblast) and gamma (immune) interferon, but alpha interferons are preferred for use in the compositions of this invention. Human alpha interferon is a naturally occurring mixture of at least eleven components including those designated $alpha_1$ and $alpha_2$ interferon, the latter being more preferred in this invention. Human alpha interferon exhibiting biological properties similar to naturally occurring alpha interferon can be made by recombinant methods. Rubenstein, *Biochem. Biophys.* Acta., 695, 5–16 (1982); Nagata et al., Nature, 284, 316320 (1980); EP 32,134; and U.S. Pat. No. 4,289,690 disclose methods for preparing $alpha_2$ interferon. Also included within the scope of this invention are the so-called alpha hydrid interferons wherein fragments of two or more native alpha interferon species are joined (See, for example, EP No. 51,873). Parenteral administration of $alpha_2$ interferon has been reported to be effective in the treatment of Kaposi's sarcoma, basal cell carcinoma, multiple myeloma and viral warts. The effective dose of alpha interferon can be easily determined by those skilled in the art.

DETAILED DESCRIPTION

The present invention relates to an insoluble complex comprising zinc, protamine and alpha interferon, as well as glycine and human serum albumin (HSA), and as such represents a complex mixture of components. While the known zinc-protamine-insulin complex is dependent on those three components for insolubilization, the zincprotamine-alpha interferon complex of the present invention also preferably comprises a second protein, HSA, in order for maximum formation of insoluble complex and surprisingly may include up to a molar excess of glycine, a zinc chelator. A preferred method for forming the insoluble complex of the present invention comprises the addition of the protamine to the solution before the zinc in order to insure that the minimum amount of soluble protein remains in the supernatant and to insure that the insoluble complex exists as fine colloidal particles which remain in dispersion for an extended period of time, rather than as large colloidal aggregates which settle easily. Another preferred method for forming the insoluble complex comprises the simultaneous addition of protamine and zinc.

Table 1 below shows the results of omitting various components and the effect of the order of addition of zinc and protamine for a composition comprising 1 mg HSA/ml, 0.1 mg alpha interferon (IFN)/ml and 20 mg glycine (G)/ml in 0.02M phosphate buffer(p). Column 1 shows the effect of the order of addition; adding zinc first results in 5% soluble protein while adding protamine first results in less than 1% soluble protein. Columns 3, 4 and 5 show that in the absence of buffer, the absence of buffer and glycine, and absence of HSA, respectively, a maximum amount of complex is not formed, since at least 5% soluble protein results in each of those combinations. While Column 2 shows that the presence of glycine is not necessary to form a complex with maximum insolubility, Column 1 shows that glycine is not detrimental to the complex despite its zinc chelating properties, as long as the protamine is added before the zinc.

TABLE 1

Dependence of Amount of Soluble Protein Found on Composition and Order of Zinc/Protamine Addition

| Order of Add'n | Comp. HSA/IFN (p/G) | HSA/IFN (p) | HSA/IFN ($H_2O$/G) | HSA/IFN ($H_2O$) | IFN ($H_2O$) |
|---|---|---|---|---|---|
| Zn/Protamine | 5% | <1% | 10% | 5% | 5% |
| Protamine/Zn | <1% | <1% | >10% | 5% | 5% |

Glycine is present in the instant invention at 0 to 50 mg/ml as a result of its presence in the lyophilized interferon preferably used to prepare the compositions of this invention. See U.S. Pat. No. 4,496,537, herein incorporated by reference, wherein a buffer, glycine and HSA are added to the interferon solutions before lyophilization to insure biological stability.

The insoluble complex formation is an equilibrium phenomenon, and as seen in Table 1, almost complete insolubilization (i.e., 99%) can be achieved in order to maximize sustained release. However, if a certain soluble fraction is desired for immediate release, the ratio of components can be changed, or preferably the pH may be adjusted. Maximum formation of insoluble complex is achieved when the interferon solution is adjusted to pH 8.0 to 8.4, preferably pH 8.2, but adjusting the pH between pH 7.5 and 8.5 will allow formation of soluble species for immediate release of alpha interferon. The following Table 2 shows the variation in complex formation due to changes in pH.

TABLE 2

INSOLUBLE COMPLEX FORMATION vs pH

| Scattering at 700 nm | pH |
|---|---|
| 0.2 | 7.0 |
| 1.12 | 7.5 |
| 2.64 | 8.0 |
| 2.64 | 8.3 |
| 2.44 | 8.4 |
| 1.80 | 8.6 |

Release of alpha interferon from the complex is not measurable in vitro since it is not solubilized by dilution, but rather by displacement of physiological chelators as well as serum albumin. The in vivo release rate can be measured by using radio-iodinated alpha interferon and monitoring the disappearance of radioactivity at the injection site and the presence of radioactivity in serum and urine. Such tests run in rats showed sustained release for more than two weeks.

The amount of alpha interferon in the formulations of the invention is $2\times10^6$ to $200\times10^6$ International Units (I.U.) per ml of complex, preferably $2\times10^7$ I.U./ml.

Zinc may be provided by 1 to 20 mg of a zinc salt/ml, wherein the zinc salt may be chosen from zinc acetate, zinc chloride or zinc sulfate, with zinc acetate being preferred.

Protamine may be provided by 0.25 to 5 mg, preferably 2.5 mg protamine/ml, wherein the protamine is chosen from protamine free base, protamine chloride, protaminen phosphate or protamine sulfate, with the sulfate being preferred.

HSA is present in a concentration range of 0 to 10 mg/ml, preferably 0.5 to 1 mg/ml.

Any chemically and pharmaceutically compatible buffer may be used to prepare the interferon solution, with phosphate buffer being preferred. Interferon solutions show maximum stability at pH 6.5 to 8.0, preferably 7.0 to 7.4 (See U.S. Pat. No. 4,496,537). Sodium hydroxide is preferred for adjusting the pH of the interferon solution to pH 7.5 to 8.5 prior to formation of the complex. The buffering agent must not have a strong affinity for zinc, as this would tend to remove zinc from the complex. This lack of affinity for zinc is especially important when glycine is present, since glycine is a zinc chelator; in the absence of glycine, some affinity for zinc by the buffer may be tolerated. A buffer with some affinity for zinc (e.g. citrate or acetate) may be used to increase the soluble fraction for immediate release of interferon.

A preferred method for preparing an insoluble complex of the present invention is to reconstitute a lyophilized alpha interferon sample prepared as described in U.S. Pat. No. 4,496,537 with a solution comprising zinc acetate and protamine sulfate at the desired pH.

Following are examples of preparations of lyophilized alpha interferon and of the reconstituted complex.

EXAMPLE 1

LYOPHILIZED ALPHA INTERFERON

| Solution for lyophilization | mg/ml |
|---|---|
| Alpha-2 Interferon | $2\times10^7$ I. U. |
| Sodium Phosphate, Dibasic, Anhydrous, Reagent | 2.27 |
| Sodium Monobasic Phosphate, USP | 0.55 |
| Glycine, USP | 20.0 |
| Albumin, Human, USP | 1.0 |
| Water for Injection, USP q.s. ad | 1.0 ml |

Charge a portion of water for Injection, USP to a suitable vessel equipped with an agitator. Consecutively charge and dissolve with agitation Sodium Phosphate, Dibasic, Anhydrous Reagent; Monobasic Sodium Phosphate, USP; Albumin, Human, USP; and Alpha-$_2$ Interferon. Bring the batch to final volume with Water for Injection, USP.

In a sterile area, aseptically filter the solution into a sterilized vessel through a sterilized 0.2 micron filter which has been washed and tested for integrity. Test the integrity of the filter after filtration.

Aseptically fill the solution into sterilized vials, load filled vials into a sterilized lyophilizer and lyophilize the solution. Aseptically stopper, seal and crimp the vials.

EXAMPLE 2

ALPHA INTERFERON COMPLEX

| Ingredients | mg/ml |
|---|---|
| Lyophilized Alpha$_2$ Interferonvial | (see Example 1) |
| Zinc acetate | 4.0 |
| Protamine sulfate | 2.5 |
| Sodium Hydroxide | 0.6 |
| Water for Injection q.s. | 1 ml |

Dissolve the lyophilized alpha$_2$ interferon in a portion of the Water for Injection. Adjust to pH 8.2 with sodium hydroxide. Add protamine sulfate and agitate; add zinc acetate and agitate. Bring the total to final volume with the remaining Water for Injection. Preferably, the sodium hydroxide, protamine sulfate and zinc acetate are added as concentrated aqueous solutions (e.g. for protamine, 100 microliters of a 25 mg/ml aqueous solution).

Bulk alpha interferon solutions (i.e., unlyophilized) or other appropriate alpha interferon samples may be used to form the complex of this invention, preferably using the same order of addition of components as described above, that is, phosphate buffer, HSA and glycine are added to aqueous alpha interferon, the pH is adjusted, protamine is added, zinc is added, and the solution is adjusted to final volume.

We claim:

1. A sustained release pharmaceutical composition comprising a parenterally acceptable insoluble zinc-protamine-alpha interferon complex, wherein the alpha interferon is present at $2\times10^6$ to $200\times10^6$ International Units/ml complex.

2. A composition of claim 1 comprising $2\times10^6$ to $200\times10^6$ International Units of alpha interferon, 1 to 20 mg of a zinc salt, 0.25 to 5 mg of protamine free base or a protamine salt, 0 to 50 mg glycine and 0 to 10 mg human serum albumin per ml of a compatible buffer at pH 7.5 to 8.5, wherein the zinc salt is selected from the group consisting of zinc acetate, zinc chloride and zinc sulfate and wherein the protamine salt is selected from the group consisting of protamine sulfate, protamine chloride and protamine phosphate.

3. A composition of claim 2 comprising zinc acetate.

4. A composition of claim 2 comprising protamine sulfate.

5. A composition of claim 2 at pH 8.0 to 8.4.

6. A composition of claim 2 comprising 4.0 mg zinc acetate, 2.5 mg protamine sulfate, 0.6 mg sodium hydroxide, 1 mg human serum albumin and 20 mg glycine per ml of solution, wherein the buffer is a phosphate buffer.

7. A composition of claim 6 comprising 2 x $10^7$ International Units of $alpha_2$ interferon.

8. A composition of claim 6 at pH 8.2.

9. A composition of claim 7 at pH 8.2.

10. A method of treating basal cell carcinoma comprising administering an amount of a composition of claim 1 effective to treat basal cell carcinoma to a mammal in need of such treatment.

* * * * *